United States Patent [19]

Stults

[11] Patent Number: 4,948,904

[45] Date of Patent: Aug. 14, 1990

[54] PROCESS FOR THE PREPARATION OF OXYDIPHTHALIC ANHYDRIDES

[75] Inventor: Jeffrey S. Stults, Grand Island, N.Y.

[73] Assignee: Occidental Chemical Corporation, Niagara Falls, N.Y.

[21] Appl. No.: 284,221

[22] Filed: Dec. 14, 1988

[51] Int. Cl.$^5$ .......................................... C07D 307/89
[52] U.S. Cl. ................................................. 549/241
[58] Field of Search ......................................... 549/241

[56] References Cited

U.S. PATENT DOCUMENTS 4,288,386  9/1981  Soula et al. ........................... 549/453
4,697,023  9/1987  Schwartz et al. ..................... 549/241
4,808,731  2/1989  Berdahl et al. ....................... 549/241

OTHER PUBLICATIONS

Gowan & Wheeler, *Name Index of Organic Reactions,* 1960, p. 244.
Morrison & Boyd, *Organic Chemistry 3rd ed.,* 1974, pp. 790–791.

*Primary Examiner*—Richard L. Raymond
*Assistant Examiner*—Raymond Covington
*Attorney, Agent, or Firm*—James F. Tao; Arthur S. Cookfair

[57] ABSTRACT

Oxydiphthalic anhydride is prepared by reacting an hydroxyphthalic anhydride with a bromophthalic or fluorophthalic anhydride and potassium fluoride in the presence of a solvent and a copper catalyst.

24 Claims, No Drawings

PROCESS FOR THE PREPARATION OF OXYDIPHTHALIC ANHYDRIDES

BACKGROUND OF THE INVENTION

This invention relates to a method for the preparation of oxydiphthalic anhydrides. The products are useful chemical intermediates for the further preparation of various compounds such as the corresponding dicarboxylic acids and the various derivatives thereof, including for example, the salts, esters, acyl halides, amides, imides and the like. The oxydiphthalic anhydrides are particularly useful as monomers in the preparation of polyimides, for example by polycondensation with a suitable diamine, such as ethylenediamine or phenylenediamine.

Various methods for the preparation of oxydiphthalic anhydrides have been described in the chemical literature. One such method, shown to be useful in the preparation of oxydiphthalic acids and anhydrides, involves the oxidation of tetramethyl diphenyl ethers. See Kolesnikov, G. S. et al, *Vysokomol. Soyed*, A9, 612-18 (1967); Marvel, C. S. et al, *J. Am. Chem. Soc.*, 80, 1197 (1958); and Latrova, Z. N. et al, *Volokna Sin. Polim.*, 15-24 (1970).

Three Japanese patents assigned to Mitsui Toatsu Chemicals, Inc describe preparations based reactions of substituted phthalic anhydrides. Japanese Patent Document 80/136,246 (Chem. Abst. 95:42680) teaches the coupling of 4-nitrophthalic anhydride in the presence of sodium nitrite or potassium nitrate to form oxydiphthalic anhydride. Japanese Patent Document 80/122, 738 (Chem. Abst. 94.83799) discloses the reaction of 4-halophthalic acid or anhydride with an alkali metal hydroxide to yield oxydiphthalic anhydride. In Japanese Patent Document 80/127, 343 (Chem. Abst. 94:191942) the reaction of 4-halo-phthalic anhydride, $Na_2CO_3$ and $NaNO_2$ in dimethyl sulfoxide to form 4,4''-dihydroxydiphthalylic anhydride is described.

German Patent 2,416,594 (1975) discloses the coupling of 3-nitrophthalic anhydride in the presence of metal nitrites, such as sodium nitrite to form oxydiphthalic anhydride.

Markezich, R. L. and Zamek, O. S., *J. Org. Chem.*, 42, 3431, (1977) describe reaction of 4-nitrophthalimide with potassium fluoride in dimethylsulfoxide to form the corresponding oxydiphthalimide which may be converted by hydrolysis to form the acid and ring closure to form the dianhydride.

SUMMARY OF THE INVENTION

It has now been found that diphthalic ether dianhydrides of the formula

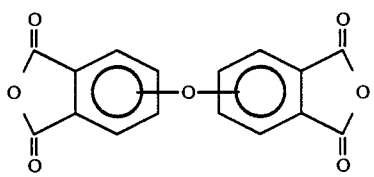

can be prepared by reacting a halo-phthalic anhydride of the formula

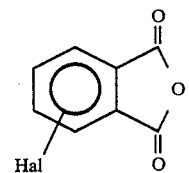

where Hal is F or Br with an hydroxyphthalic anhydride of the formula

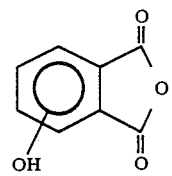

and an alkali metal compound selected from the group KF and CsF in the presence of a solvent and a copper catalyst.

In the process of the invention, the ether bridge is formed at the site of the halo- and hydroxy-substituents on the phthalic anhydride reactants. Thus, when the substituents of both reactants are at the 4-position, i.e., 4-halophthalic anhydride and -hydroxyphthalic anhydride, the oxydiphthalic product will be 4,4'-oxydiphthalic anhydride, characterized by the formula

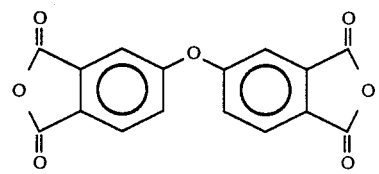

When both reactants are 3-substituted, that is, when the reactants are 3-halophthalic anhydride and 3-hydroxyphthalic anhydride, the oxydiphthalic product will be 3,3'-oxydiphthalic anhydride characterized by the formula

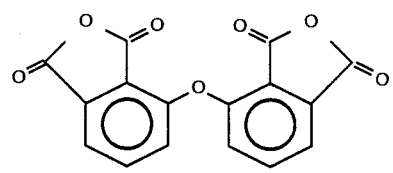

Alternatively, a mixture of 3-substituted and 4-substituted phthalic anhydrides, such as 3-halophthalic anhydride and 4-hydroxyphthalic anhydride or 4-halophthalic anhydride and 3-hydroxyphthalic anhydride may be employed to prepare a 3,4-oxydiphthalic anhydride of the formula

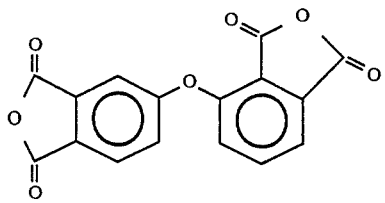

The halogen substituent on the starting halophthalic anhydride reactant may be F or Br, the preferred reactant being fluorophthalic anhydride.

Suitable copper catalysts that may be employed in the process of this invention include elemental copper, cuprous oxide, cupric oxide, copper chromite, bis[copper (I) trifluoromethanesulfonate], benzene complex (i.e., copper (I) triflate), copper (II) trifluoromethanesulfonate (i.e., copper (II) triflate), copper (I) bromide (most conveniently as a stabilized complex, such as copper (I) bromide-dimethylsulfide complex), copper sulfate, cupric tetrafluoroborate and cuprous benzoate.

The alkali metal compound may be potassium carbonate, potassium fluoride, or cesium fluoride. Although potassium carbonate may be used, it is not generally preferred, because its use tends to generate undesired side products. The proportions of reactants may vary considerably, however, it is recommended that the alkali metal compound be employed in sufficient proportions to provide at least about one equivalent of potassium (or cesium) per mole of halo-phthalic anhydride. Preferably the alkali metal compound is employed in substantial excess, for example, up to about 50 percent excess, of the aforesaid equivalent proportions. Furthermore, it is recommended that the reaction be carried out under anhydrous conditions, to minimize the occurrence of undesired side reactions.

The process of the invention is preferably carried out at atmospheric pressure, but super-atmospheric pressure, for example, under autogeneous conditions, may be employed, if desired. The process may be carried out neat, but is preferably carried out in the presence of a solvent. Suitable solvents include both apolar and polar solvents, the preferred solvents being polar, aprotic solvents such as N,N-dimethyl formamide, dimethyl acetamide, triglyme, sulfolane, N-methyl-pyrrolidone, or the like. When an apolar solvent is employed, it has been found preferable to also employ a phase transfer catalyst, such as a crown ether or phosphonium salt.

The temperature at which the process is carried out may vary considerably, but will generally be within the range of about 110° to about 220° Celsius. Higher or lower temperature may be employed but are less efficient. The choice of solvent may govern the temperature employed. For example, at atmospheric conditions the boiling point of the solvent becomes a limiting condition. Moreover, the decrease in efficiency of the reaction as the temperature is lowered, varies somewhat with the solvent. For example, the preferred temperature, when using sulfolane as the solvent, is in the range of about 160° -215° and, most preferably, about 170° -200° Celsius.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

A suspension of potassium fluoride (6.4 g), 4-fluorophthalic anhydride (16.6 g), 4-hydroxyphthalic anhydride (16.6 g), and red cuprous oxide (0.8 g) in anhydrous DMF (66 ml) was heated to 110° C. and maintained thereat with stirring for 95 minutes. The suspension was then filtered and collected solid, washed with N,Ndimethyl formamide and the solvent removed by evaporation under reduced pressure in a rotary evaporator. The remaining brown solid was dissolved in refluxing 1,2,4-trichlorobenzene (100 ml) and then allowed to cool. The resulting precipitate was collected by filtration. After washing with additional trichlorobenzene, the solid was further washed with hexanes and dried to give oxydiphthalic as a slightly off-white solid (30.8 g; 99 percent yield).

The general procedure of the foregoing example was repeated using various copper catalysts varying the reaction conditions and the amount of reactants as shown in the following table. Reaction products were analyzed by gas chromatography with the results as shown in the table.

TABLE 1

| REACTANTS & CONDITIONS | EXAMPLES | | | | | | | | | | | |
|---|---|---|---|---|---|---|---|---|---|---|---|---|
| | 2 | 3 | 4 | 5 | 6 | 7 | 8 | 9 | 10 | 11 | 12 | 13 |
| 4-Fluorophthalic Anhydride (g) | 0.37 | 0.38 | 0.51 | 0.36 | 0.38 | 0.37 | 0.37 | 0.45 | 0.47 | 0.51 | 0.52 | 0.50 |
| 4-Hydroxyphthalic Anhydride (g) | 0.36 | 0.38 | 0.51 | 0.39 | 0.37 | 0.34 | 0.38 | 0.53 | 0.46 | 0.52 | 0.50 | 0.49 |
| Potassium Fluoride (g) | | | | 0.20 | 0.20 | 0.20 | 0.20 | 0.24 | 0.20 | 0.22 | 0.22 | 0.20 |
| Dimethyl Formamide (ml) | 3.0 | 3.0 | 4.0 | 4.0 | 4.0 | 4.0 | 4.0 | 4.4 | 5.8 | 5.1 | 4.0 | 4.0 |
| Copper Catalysts: | | | | | | | | | | | | |
| None (*) | * | | | * | | | | * | | | * | |
| CuSO$_4$ 2H$_2$O (g) | | 0.1 | | | | | | | | | | |
| CuO (g) | | | | | 0.03 | | | | | | | |
| Copper chromite (g) | | | | | | 0.03 | | | | | | |
| (CH$_3$)$_2$S CuBr (g) | | | | | | | 0.04 | | | | | |
| Cu(BF$_4$)$_2$ | | | | | | | | | 0.05 | | | |
| Copper (I) triflate | | | | | | | | | | 0.05 | | |
| Copper (II) triflate | | | 0.1 | | | | | | | | | |
| Copper benzoate | | | | | | | | | | | 0.03 | |
| Reaction Period (hours) | 0.4 | 0.4 | 0.4 | 0.3 | 0.3 | 0.3 | 0.3 | 2.1 | 2.1 | 2.1 | 0.7 | 0.7 |
| Temperature (°C.) | 115 | 115 | 115 | 120 | 120 | 120 | 120 | 115 | 115 | 115 | | |
| Yield of Oxydiphthalic Anhydride (GC Area Percent) | 23.0 | 41.8 | 41.1 | 13.6 | 42.9 | 41.6 | 27.1 | 41.6 | 51.3 | 63.0 | 34.8 | 43.1 |

TABLE 2

| REACTANTS & CONDITIONS | EXAMPLES | | | | | | | | | | |
|---|---|---|---|---|---|---|---|---|---|---|---|
| | 14 | 15 | 16 | 17 | 18 | 19 | 20 | 21 | 22 | 23 | 24 |
| 4-Fluorophthalic Anhydride (g) | | | | | | | | | 0.30 | 0.60 | |
| 4-Chlorophthalic Anhydride (g) | | | | | | | | | | | 0.95 |
| 4-Bromophthalic Anhydride (g) | 0.49 | 0.49 | 0.45 | 0.45 | 0.46 | 0.46 | 0.46 | 0.46 | | | |
| 4-Hydroxyphthalic Anhydride (g) | 0.52 | 0.51 | 0.33 | 0.32 | 0.33 | 0.33 | 0.33 | 0.32 | 0.30 | 0.60 | 0.87 |
| Potassium Fluoride (g) | 0.19 | 0.19 | 0.27 | 0.27 | 0.26 | 0.26 | 0.27 | 0.27 | 0.20 | 0.40 | 0.33 |
| Dimethyl Formamide (ml) | | | | | | | | | | | 9.3 |
| Sulfolane (ml) | 4.0 | 4.0 | 2.5 | 2.5 | 2.5 | 2.5 | 2.0 | 2.0 | | | |
| Cymene (ml) | | | | | | | | | 2.0 | 4.0 | |
| Tetraphenylphosphonium Chloride (g) | | | | | | | | | 0.09 | 0.18 | |
| Copper Catalysts: | | | | | | | | | | | |
| None (*) | * | | * | | | | * | | * | | |
| Cu$_2$O (g) | | 0.05 | | 0.02 | | | | | | 0.33 | |
| Copper (I) triflate | | | | | 0.02 | | | 0.02 | | | |
| Copper (I) benzoate | | | | | | 0.03 | | | | | 0.02 |
| Reaction Period (hours) | 1.0 | 1.0 | 1.4 | 2.0 | 1.2 | 1.3 | 0.25 | 0.25 | 4.0 | 4.0 | 4.0 |
| Temperature (°C.) | 160 | 160 | 180 | 170 | 170 | 163 | 200 | 200 | Reflux | Reflux | Reflux |
| Yield of Oxydiphthalic Anhydride (GC Area Percent) | 50.0 | 70.0 | 50.0 | 70.0 | 70.0 | 50.0 | 80.0 | 80.0 | 50.0 | 56.0 | 0 |

I claim:

1. A process for the preparation of a diphthalic ether dianhydride of the formula

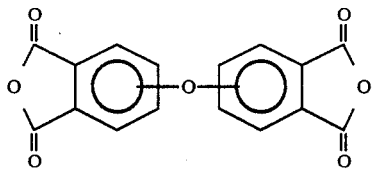

comprising reacting a halo-phthalic anhydride of the formula

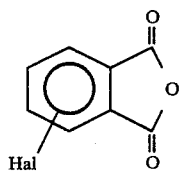

where Hal is F or Br, with an hydroxyphthalic anhydride of the formula

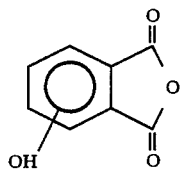

and an alkali metal compound from the group consisting of K$_2$CO$_3$, KF, and CsF in the presence of a copper catalyst from the group consisting of elemental copper, cuprous oxide, cupric oxide, copper chromite, copper sulfate, copper (I) triflate, copper (II) triflate, stabilized copper (I) bromide, cupric tetrafluoroborate, cuprous benzoate and mixtures thereof.

2. A process according to claim 1 wherein the alkali metal compound is potassium fluoride.

3. A process according to claim 2 wherein the halophthalic anhydride is fluorophthalic anhydride.

4. A process according to claim 2 wherein the halophthalic anhydride is bromophthalic anhydride.

5. A process according to claim 2 carried out in the presence of a polar, aprotic solvent.

6. A process according to claim 5 wherein the solvent is sulfolane or N,N-dimethyl formamide.

7. A process according to claim 2 wherein the copper catalyst is cuprous oxide.

8. A process according to claim 2 wherein the copper catalyst is cupric oxide.

9. A process according to claim 2 wherein the copper catalyst is copper (I) triflate.

10. A process according to claim 2 wherein the copper catalyst is copper (II) triflate.

11. A process according to claim 2 wherein the copper catalyst is copper (I) bromide, dimethyl sulfide complex.

12. A process according to claim 2 wherein the copper catalyst is cuprous benzoate.

13. A process according to claim 2 wherein the copper catalyst is copper sulfate.

14. A process according to claim 2 wherein the copper catalyst is elemental copper.

15. A process for the preparation of 4,4''-oxydiphthalic anhydride which comprises reacting a 4 halophthalic anhydride selected from 4-bromophthalic anhydride and 4-fluorophthalic anhydride with 4-hydroxyphthalic anhydride and an alkali metal compound selected from potassium fluoride and cesium fluoride and in the presence of a copper catalyst selected from elemental copper, cuprous oxide, cupric oxide, copper chromite, copper (I) triflate-benzene complex, copper (II) triflate, stabilized copper (I) bromide, copper sulfate, cupric tetrafluoroborate, cuprous benzoate and mixtures thereof.

16. A process according to claim 15 wherein the 4-halophthalic anhydride is 4-fluorophthalic anhydride.

17. A process according to claim 15 wherein the 4-halophthalic anhydride is 4-bromophthalic anhydride.

18. A process according to claim 15 wherein the alkali metal compound is potassium fluoride.

19. A process according to claim 15 carried out in the presence of a solvent.

20. A process according to claim 19 wherein the solvent is selected from the group consisting of sulfolane, N,N-dimethylformamide, and cymene.

21. A process according to claim 20 wherein the solvent is cymene and the process is carried out in the presence of a phase transfer agent.

22. A process according to claim 21 wherein the phase transfer agent is tetraphenylphosphonium chloride.

23. A process according to claim 15 carried out at a temperature of about 110° to about 220° Celsius.

24. A process for the preparation of 4,4'-oxydiphthalic anhydride comprising reacting a 4-halophthalic anhydride wherein halo- is fluoro- or bromo- with 4-hydroxyphthalic anhydride and potassium fluoride in the presence of a solvent at a temperature of about 110° to about 220° Celsius in the presence of a catalyst selected from elemental copper, cuprous oxide, cupric oxide, copper chromite, copper (I) triflate-benzene complex, copper (II) triflate, copper (I) bromide-dimethylsulfide complex, copper sulfate, cupric tetrafluoroborate, cuprous benzoate and mixtures thereof.

* * * * *